(12) United States Patent
Den Braber et al.

(10) Patent No.: US 8,742,206 B2
(45) Date of Patent: Jun. 3, 2014

(54) MULTILEAF SPINACH

(75) Inventors: Jan Hugo Den Braber, Klundert (NL); Beatrice Ingrid Lindhout, Dordrecht (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 637 days.

(21) Appl. No.: 12/977,162

(22) Filed: Dec. 23, 2010

(65) Prior Publication Data

US 2012/0054894 A1 Mar. 1, 2012

(30) Foreign Application Priority Data

Aug. 26, 2010 (NL) ...................................... 2005279

(51) Int. Cl.
| | | |
|---|---|---|
| *A01H 1/04* | (2006.01) | |
| *A01H 5/12* | (2006.01) | |
| *C12N 5/04* | (2006.01) | |
| *C12Q 1/68* | (2006.01) | |
| *A01D 46/00* | (2006.01) | |
| *A01D 46/28* | (2006.01) | |
| *B65B 25/02* | (2006.01) | |
| *A23L 1/212* | (2006.01) | |

(52) U.S. Cl.
USPC .......... 800/298; 800/266; 435/410; 435/6.11; 47/58.1 FV; 426/392

(58) Field of Classification Search
None
See application file for complete search history.

(56) References Cited

U.S. PATENT DOCUMENTS

| | | |
|---|---|---|
| 5,859,338 A | 1/1999 | Meyerowitz et al. |
| 2013/0243931 A1 | 9/2013 | Baerends |

OTHER PUBLICATIONS

Gonzalez—Spinach Studies—1989.*
Asgrow_Seed for Today_pp. 124-27_1980.*
Harris Seeds—p. 38—1992.*
Park Seed—p. 108—2001.*
Varalakshmi—J Hortl. Sci May 21, 2010.*
Magruder et al., USDA Publication No. 316, 1938.*
Al-Khayri—In Vitro Cell Dev Biol—28P—64—1992.*
Moreloc—Spinach—2008.*
Brantsandpatents Oct. 11, 2013 Letter to European Patent Office concerning EP 2 608 657 ("the Brantsandpatents EPO letter"), and citing Spinach variety POH 0211 and US Patent No. 5,859,338 and including Pop Vriend Seeds B.V. (NL) invoice 5502127 to Kaneko Seeds Co. Ltd (JP).

* cited by examiner

*Primary Examiner* — David H Kruse
*Assistant Examiner* — Russell Boggs
(74) *Attorney, Agent, or Firm* — Vedder Price P.C.; Thomas J. Kowalski; Deborah L. Lu (57) ABSTRACT

Spinach having significantly more leaves per plant as compared to known spinach and, inter alia, cells of these plants, seeds and other propagation material as well as harvestable parts of these plants, and methods for obtaining, and using and uses of these plants and parts thereof.

66 Claims, 3 Drawing Sheets

MULTILEAF SPINACH

RELATED APPLICATIONS & INCORPORATION BY REFERENCE

Mention is made of, and to the extent permissible priority is claimed from, Netherlands patent application Serial No. 2005279, filed Aug. 26, 2010.

The foregoing application(s), and all documents cited therein or during the prosecution of the foregoing applications(s) ("appln cited documents") and all documents cited or referenced in the appln cited documents, and all documents cited or referenced herein ("herein cited documents"), and all documents cited or referenced in herein cited documents, together with any manufacturer's instructions, descriptions, products specifications, and product sheets for any products mentioned herein or in any document incorporated herein by reference, are hereby incorporated herein by reference, and may be employed in the practice of the invention.

FIELD OF THE INVENTION

The present invention relates to a new type of spinach (*Spinacia oleracea*) plant, a "multileaf trait" spinach plant—a new type of spinach plant that has substantially more leaves per plant as compared to existing spinach plants—and to, inter alia, cells of these plants, seeds and other propagation material as well as harvestable parts of these plants, and methods for obtaining, and using and uses of these plants and parts thereof.

BACKGROUND OF THE INVENTION

Spinach (*Spinacia oleracea*) is a flowering plant in the family of Amaranthaceae that is grown as a vegetable. The consumable parts of spinach are the leaves from the vegetative stage. Spinach is sold loose, bunched, in prepackaged bags, canned, or frozen.

There are three basic types of spinach, namely savoy, semi-savoy and smooth. Savoy has dark green, crinkly and curly leaves. Flat or smooth leaf spinach has broad smooth leaves. Semi-savoy is a variety with slightly crinkled leaves. The main market for spinach is baby-leaf. Baby spinach leaves are usually of the flat-leaf variety and no longer than about eight centimeter. These tender, sweet leaves are sold loose rather than in bunches. It is often used in salads, but can also be lightly cooked.

Citation or identification of any document herein is not an admission that such document is available as prior art against the present invention.

SUMMARY OF THE INVENTION

The present inventors have now developed a new type of spinach plant that has substantially more leaves per plant as compared to existing spinach plants. This highly increases the efficiency of spinach production as more leaves can be harvested per seed. The substantially more leaves per plant are found in the vegetative plant stage, at which the plants are harvested for consumption.

The new trait, which is called herein the "multileaf trait" is as found in plants of which representative seeds are deposited on 29 Apr. 2009 with NCIMB Ltd, Ferguson Building, Craibstone Estate, Bucksburn, Aberdeen AB21 9YA, UK under deposit accession number NCIMB 41619.

The new multileaf trait can be defined as having at least 1.25 times, preferably at least 1.5 times, more preferably at least 2 times, most preferably at least 2.5 times as many leaves per plant as a plant that does not carry the multileaf trait. The comparison is made between plants in the same developmental stage. Suitably this stage is the vegetative plant stage (approx. 7 weeks after sowing).

The multileaf trait of the invention can be introduced into any other spinach plant, irrespective of leaf type (smooth, semi-savoy or savoy) or leaf morphology (smooth, weakly to strongly incised) or any other characteristic.

The present invention relates to a new type of spinach (*Spinacia oleracea*) plant; a "multileaf trait" spinach. The invention further relates to a part or tissue culture of this new "multileaf trait" spinach plant, including a cell or protoplast from this new spinach plant, such as an embryo, meristem, cotyledon, pollen, leaf, anther, root, root tip, pistil, flower, seed or stalk. The invention particularly involves cells, seeds and other propagation material of or from this new type of spinach, as well as harvestable parts of this new type of spinach, especially leaves from the vegetative stage.

The invention further comprehends such leaves in packaged form, including without limitation such leaves in prepackaged spinach salad or as canned spinach or as frozen spinach. Mention is made of U.S. Pat. No. 5,523,136, incorporated herein by reference consistent with the above RELATED APPLICATIONS & INCORPORATION BY REFERENCE section, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the new type of spinach.

The invention yet further relates to a spinach plant having all the physiological and morphological characteristics of the "multileaf trait" new type of spinach plant of the invention, representative seed of which having been deposited under NCIMB Accession No. NCIMB 41619.

The invention accordingly comprehends a seed of "multileaf trait" spinach, representative seed of said line having been deposited under NCIMB Accession No. NCIMB 41619, as well as a plant grown from that seed, and a part of that plant. The plant part can be selected from the group consisting of pollen, an ovule and a cell. Likewise, the invention involves a tissue culture of regenerable cells of "multileaf trait" spinach, representative seed of which having been deposited under NCIMB Accession No. NCIMB 41619, and the tissue culture can comprise cells or protoplasts from a plant part selected from the group consisting of embryos, meristems, cotyledons, pollen, leaves, anthers, roots, root tips, pistil, flower, seed and stalks. Also, the invention provides a spinach plant regenerated from the tissue culture, wherein the regenerated plant expresses all of the physiological and morphological characteristics of "multileaf trait" spinach, representative seed of which having been deposited under NCIMB Accession No. NCIMB 41619.

The invention additionally relates to progeny of the new type of spinach, for instance, such progeny that exhibits physiological and morphological characteristics of the new type of spinach, representative seed of which having been deposited under NCIMB Accession No. NCIMB 41619, e.g., progeny that exhibits all of the physiological and morphological characteristics of the new type of spinach, representative seed of which having been deposited under NCIMB Accession No. NCIMB 41619. For example, the invention comprehends a progeny plant of a plant grown from a "multileaf trait" spinach seed, representative seed of which having been deposited under NCIMB Accession No. NCIMB 41619, that comprises all of the physiological and morphological characteristics of "multileaf trait" spinach, representative seed of which having been deposited under NCIMB Accession No. NCIMB 41619. And of course, the invention comprehends seed that produces such a plant. The invention additionally comprehends a method of producing spinach seed, comprising crossing a "multileaf trait" spinach plant (e.g., a spinach plant grown from seed of "multileaf trait" spinach, representative seed of said line having been deposited under NCIMB Accession No. NCIMB 41619 and/or a spinach plant that exhibits all of the physiological and morphological characteristics of the new type of spinach, representative seed of which having been deposited under NCIMB Accession No. NCIMB 41619) with a second spinach plant. In such a method the "multileaf trait" spinach plant can be a female plant. The invention also encompasses F1 hybrid seed produced by such a method as well as an F1 hybrid plant produced by growing the F1 hybrid seed.

Accordingly, the invention also relates to spinach plants obtainable by crossing a first spinach parent plant with a second spinach parent plant that has the "multileaf trait" as found in plants of which representative seed was deposited under deposit accession number NCIMB 41619 to obtain F1 plants, subsequently selfing plants of the F1 to obtain the F2 generation and selecting plants from the F2 that have the multileaf trait as found in plants of which representative seed was deposited under deposit accession number NCIMB 41619.

Also, the invention comprehends methods for producing a seed of a "multileaf trait"-derived spinach plant comprising (a) crossing a "multileaf trait" spinach plant, representative seed of which having been deposited under NCIMB Accession No. NCIMB 41619, with a second spinach plant, and (b) whereby seed of a "multileaf trait"-derived spinach plant form (e.g., by allowing the plant from the cross to grow to producing seed). Such a method can further comprise (c) crossing a plant grown from "multileaf trait"-derived spinach seed with itself or with a second spinach plant to yield additional "multileaf trait"-derived spinach seed, (d) growing the additional "multileaf trait"-derived spinach seed of step (c) to yield additional "multileaf trait"-derived spinach plants, and (e) repeating the crossing and growing of steps (c) and (d) to generate further "multileaf trait"-derived spinach plants.

The invention also relates to a method of vegetatively propagating a plant of "multileaf trait" spinach comprising the steps of: (a) collecting tissue capable of being propagated from a plant of a "multileaf trait" spinach plant, representative seed of which having been deposited under NCIMB Accession No. NCIMB 41619; (b) cultivating said tissue to obtain proliferated shoots; and (c) rooting said proliferated shoots to obtain rooted plantlets. This method can further comprise growing plants from the rooted plantlets.

The invention additionally provides a method of introducing a desired trait into "multileaf trait" spinach comprising: (a) crossing a "multileaf trait" spinach plant, representative seed of which having been deposited under NCIMB Accession No. NCIMB 41619, with a second spinach plant that comprises a desired trait to produce F1 progeny; (b) selecting an F1 progeny that comprises the desired trait; (c) crossing the selected F1 progeny with a "multileaf trait" spinach plant, to produce backcross progeny; (d) selecting backcross progeny comprising the desired trait and the physiological and morphological characteristic of a "multileaf trait" spinach plant; and (e) repeating steps (c) and (d) three or more times in succession to produce selected fourth or higher backcross progeny that comprise the desired trait and all of the physiological and morphological characteristics of a "multileaf trait" spinach plant, when grown in the same environmental conditions. The invention, of course, includes a spinach plant produced by this method.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When "multileaf trait" spinach, e.g. a spinach plant a representative seed of which having been deposited under NCIMB Accession No. NCIMB 41619, is used in backcrossing, offspring retaining the "multleaf trait" are progeny within the ambit of the invention. Backcrossing methods can be used with the present invention to improve or introduce a characteristic into the multileaf trait spinach plant of the invention. See, e.g., U.S. Pat. No. 7,705,206 (incorporated herein by reference consistent with the above RELATED APPLICATIONS & INCORPORATION BY REFERENCE section), for a general discussion relating to backcrossing.

The invention also provides a method of producing a "multileaf trait" spinach plant, representative seed of which having been deposited under NCIMB Accession No. NCIMB 41619, comprising an added desired trait, the method comprising introducing a transgene conferring the desired trait into a "multileaf trait" spinach plant.

The invention further involves a method of determining the genotype of a "multileaf trait" spinach plant, representative seed of which having been deposited under NCIMB Accession No. NCIMB 41619, or a first generation progeny thereof, comprising obtaining a sample of nucleic acids from said plant and detecting in said nucleic acids a plurality of polymorphisms. This method can additionally comprise the step of storing the results of detecting the plurality of polymorphisms on a computer readable medium. The plurality of polymorphisms are indicative of and/or give rise to the expression of the "multileaf trait".

The invention even further relates to a method of producing spinach comprising: (a) cultivating to the vegetative plant stage a "multileaf trait" spinach plant, representative seed of which having been deposited under NCIMB Accession No. NCIMB 41619, and (b) harvesting spinach from the plant. The invention further comprehends canning, freezing or packaging the spinach.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

Deposit

The Deposit with NCIMB Ltd, Ferguson Building, Craibstone Estate, Bucksburn, Aberdeen AB21 9YA, UK, under deposit accession number NCIMB 41619 was made pursuant to the terms of the Budapest Treaty. Upon issuance of a patent, all restrictions upon the deposit will be removed, and the deposit is intended to meet the requirements of 37 CFR §1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following Detailed Description, including the Examples, given by way of example, but not intended to limit the invention solely to the specific embodiments described, may be best understood in conjunction with the accompanying drawings, incorporated herein by reference, in which.

DETAILED DESCRIPTION OF THE INVENTION

The New "Multileaf Trait" Spinach of the Invention

The invention relates to a new type of spinach plants that have significantly more leaves per plant as compared to known spinach plants.

The greenhouse trials in which the multileaf trait was investigated were performed in different growing seasons including August, October, and January. Independently of the growing season the multileaf type produced significantly more leaves as compared to the controls.

When plants were harvested at baby-leaf stage, i.e. an earlier developmental stage, spinach plants of the multileaf type already produced significantly more leaves than the controls. The trait is thus independent of the developmental stage. However, the multileaf trait is based on comparison between plants that are in substantially the same developmental stage, in particular the vegetative stage, more in particular approximately 7 weeks after sowing. Thus, at substantially the same developmental stage spinach plants of the invention carrying the multileaf trait have a higher number of leaves than spinach plants not carrying the multileaf trait.

Moreover, it was found in multileaf spinach plants that the rate of leaf emergence is accelerated in comparison to other spinach plants not carrying the multileaf trait and grown simultaneously at equal conditions.

In an embodiment, the invention relates to a spinach plant which carries the multileaf trait and has at least 1.25 times as many leaves as a spinach plant not carrying the multileaf trait. The trait is obtainable or can be or is obtained by introgression from a spinach plant, representative seed of which was deposited with the NCIMB under accession number NCIMB 41619.

In an embodiment, the trait is introduced into the spinach plant from a spinach plant grown from seed that was deposited with the NCIMB under accession number NCIMB 41619, or from a progeny plant thereof.

In an embodiment, the invention relates to a spinach plant that carries the multileaf trait and has at least 1.25 times as many leaves as a spinach plant not carrying the multileaf trait wherein the trait is introgressed from a plant, representative seed of which was deposited with the NCIMB under accession number NCIMB 41619.

Introgression

In an embodiment, the trait is introgressed from a plant grown from seed that was deposited with the NCIMB under accession number NCIMB 41619 or a progeny plant thereof.

"Introgression" as used herein is intended to mean introduction of a trait into a plant not carrying the trait by means of crossing and selection.

It is noted that if the selection criterion or criteria is or are clearly defined, the skilled person will be able to identify the descendants that carry the trait in any further generation. For the trait of the invention descendants from a cross between a plant not carrying the multileaf trait and a plant carrying the multileaf trait as found in plants of which representative seeds was deposited under accession number NCIMB 41619 can be identified by growing F2 plants from seeds that are the result from the initial cross and a selfing step, selecting plants exhibiting the multileaf trait, i.e. that produce leaves as plants having the multileaf trait, e.g., that produce leaves as plants grown from seed deposited under deposit accession number NCIMB 41619 (as such seed is representative of seeds of plants that exhibit the multileaf trait).

Crossing

In an embodiment, the invention relates to spinach plants obtainable by crossing a first spinach parent plant with a second spinach parent plant that has the multileaf trait as found in plants of which representative seed was deposited under deposit accession number NCIMB 41619 to obtain an F1, subsequently selfing plants of the F1 to obtain an F2 and selecting plants from the F2 that have the multileaf trait as plants of the invention. The multileaf trait is transferred in a pattern consistent with recessive inheritance.

Selection of spinach plants for breeding therefore can also be independent of the phenotype of a plant and instead can be based on genetic investigations. For example, one can utilize a suitable genetic marker which is closely genetically linked to a trait of interest—the multileaf trait in this instance, e.g., as identified using seed deposited under deposit accession number NCIMB 41619. These markers can be used to identify the presence of the trait in the offspring of a particular cross (e.g., two heterozygous plants that carry the genetic information for the multileaf trait but do not have that phenotype because it is recessive and they are not homozygous therefor), and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Methods for marker assisted selection are of particular utility in the case of recessive traits and variable phenotypes, or where conventional assays may be more expensive, time consuming or otherwise disadvantageous, and types of genetic markers which could be used in accordance with the invention include, but are not necessarily limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs). Reference is made to U.S. Pat. No. 7,705,206, for documents and a discussion relating to the foregoing methods; and, U.S. Pat. No. 7,705,206, and the documents cited therein, including as to the foregoing methods, are hereby incorporated herein by reference consistent with the above RELATED APPLICATIONS & INCORPORATION BY REFERENCE section.

In an embodiment the second spinach parent plant is a plant grown from the deposited seeds.

In an embodiment the second spinach parent plant is a progeny plant of a plant grown from the deposited seeds.

In an embodiment the second spinach parent plant is a plant having the genetic information that encodes the multileaf phenotype.

In an embodiment this genetic information is substantially identical to the genetic information that encodes the multileaf trait as found in plants of which representative seeds were deposited under deposit accession number NCIMB 41619, in particular plants grown from seeds as deposited under deposit accession number 41619 (wherein "substantially identical" is identical to the genetic information in the seeds deposited under NCIMB 41619, or so similar to the genetic information in the seeds deposited under NCIMB 41619 at the locus or gene that gives rise to expression of the multileaf trait phenotype in the seeds deposited under deposit number 41619 such that the sample also has the multileaf trait, e.g., a sample can be "substantially identical" in its genome to seeds deposited under deposit number 41619 because it is different than the genome of seeds deposited under deposit number 41619 due to the degeneracy of the genetic code).

In an embodiment, the invention thus relates to a spinach plant, showing the trait multileaf, which plant is obtainable by:
  a) growing plants representative seed of which was deposited under NCIMB number 41619;
  b) crossing a plant from step a) with a spinach plant that does not have the multileaf trait to obtain an F1 population;
  c) selfing plants from the F1 to obtain a F2 population; and
  d) identifying plants showing the multileaf trait in the F2 population as multileaf spinach plants.

In the method described above steps c) and d) can be repeated one or more times by selfing an Fn population to obtain an Fn+1 population and identifying plants showing the multileaf trait in the Fn+1 population as multileaf spinach plants.

Genotype

The multileaf trait is phenotypically visible because plants form significantly more leaves. The trait is however caused by the plant's genotype. The genotype as far as it concerns the multileaf trait is the same as or substantially similar or identical to genotype as found in the deposited seeds. On a nucleic acid molecule basis, this can mean a first nucleic acid molecule having at least 95, 96, 97, 98 or 99 percent identity with a second nucleic molecule, wherein the second acid molecule is of a herein identified or exemplified or deposited plant, plant part, seed, cell or the like, and the expression of both the first and second nucleic acid molecules in a spinach plant results in the phenotype of the multileaf trait. The part of the genotype of a spinach plant that causes the multileaf trait will be called herein the "genetic information that encodes the multileaf trait". Presence of this genetic information is phenotypically visible and plants having this genetic information can thus be selected on the basis of this phenotypic expression of the underlying gene or genes.

As used herein "genetic information" is intended to mean the portion of the genome, e.g. gene or genes, that are responsible for the formation of significantly more leaves; which portion of the genome can be detected in the genome, e.g. by detecting polymorphisms in the genome of "multileaf trait" plants of which representative seed was deposited under deposit accession number NCIMB 41619, and that portion of the genome, particularly the portion that gives rise to expression of the "multileaf trait" can thus be isolated from the genome and can be an isolated nucleic acid molecule encoding the multileaf trait (which when introduced into the genome of a regenerable cell of a spinach plant that does not carry this genotype and when in the cell operably linked to and under the control of a suitable promoter, gives rise to the expression of the "multileaf trait" in a spinach plant regenerated from a tissue culture of such regenerable cells into which the isolated nucleic acid molecule has been introduced and is present in the cells operably linked to and under the control of a suitable promoter).

The presence of the genetic information that is responsible for the multileaf trait of the invention in the genome of a plant that shows a multileaf characteristic can be determined with the following test: The plant to be tested should be or should be made to be homozygous for the genetic information responsible for the multileaf trait. The skilled person knows how to obtain a plant that is homozygous for the trait to be tested, e.g., via selfing or self mating or self crossing. This homozygous plant is then crossed with a tester plant that carries the genetic information that is responsible for the trait of the invention in homozygous condition. If the plant to be tested has a multileaf characteristic as a result of the same genetic information that is responsible for the trait of the invention, all progeny plants of this first cross and successive generations will express the trait. If the multileaf characteristic of the plant to be tested is the result of a different part of the genome, e.g. another gene or locus, segregation will occur. The tester plant can be any plant that carries the genetic information of the invention in homozygous condition, such as plants of which representative seed was deposited under accession number NCIMB 41619 or plants directly grown from the deposited seeds or progeny thereof that has retained the trait.

In an embodiment of the invention a spinach plant is provided that comprises the multileaf trait and thus when crossed with a tester plant, that comprises the multileaf trait of the invention and representative seed of which as deposited with the NCIMB under accession numbers a NCIMB 41619, or a progeny plant thereof that comprises the multileaf trait comprised in spinach plants representative seed of which was deposited with the NCIMB under accession number NCIMB 41619 or a plant derived therefrom and comprising the multileaf trait, plants of the first generation progeny (F1) of said cross show a 1:0 segregation for the multileaf trait. In both the tester plant and the plant of the invention the multileaf trait is present in homozygous condition. Plants of the second and further generations, if obtained by selfing also show a 1:0 segregation for the multileaf trait. The tester plant can be a plant of which representative seed was deposited with the NCIMB under accession number NCIMB 41619. When the genetic information responsible for the multileaf trait as contained in the deposit is present in a plant, the plant is a plant of the invention (and seeds therefrom are seeds of the invention, plant parts thereof are plant parts of the invention, etc.).

The multileaf characteristic of the invention has a genetic basis in the genome of the spinach plant. With the above described cross with a tester plant, plants can be identified as being plants of the invention.

The multileaf trait is independent of other traits of a spinach plant. The trait can thus occur in spinach plants that are completely different in all their other characteristics, for example in different spinach varieties.

The deposited spinach seeds contain in their genome the genetic information that encodes the multileaf trait. The deposited seeds are thus a source for the genetic information that leads to the trait. The skilled person is capable of introducing the trait into any other spinach plant he desires. A plant resulting from the initial cross between a first spinach parent plant with a second spinach parent plant that contains the genetic information responsible for the multileaf trait, cannot yet be identified as being a plant of the invention. Therefore, an F2 generation is produced by selfing plants of the F1 and assessing the number of leaves of the F2 progeny plant and comparing it with the number of leaves of the first parent plant. If this number is at least 1.25 times higher than the number of leaves in the first parent plant, the progeny plant is a plant of the invention.

In one embodiment, the source from which the genetic information is acquired is formed by plants grown from the deposited seeds or sexual or vegetative descendants therefrom.

It is clear, however, that a parent that provides the trait of the invention is not necessarily a plant grown directly from the deposited seeds. For example, the parent can also be a progeny plant from the seed or a progeny plant from seeds that are identified to have or to have acquired the trait of the invention by other means.

Introducing Trait or Additional Traits

In an embodiment, the invention relates to spinach plants that carry the trait of the invention and have acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into a multileaf trait spinach plant of the invention, by genetic transformation techniques; and, such multileaf spinach plants that have additional genetic information introduced into the genome or that express additional traits by having the DNA coding therefor introduced into the genome via transformation techniques, are within the ambit of the invention, as well as uses of such plants, and the making of such plants.

Genetic transformation may therefore be used to insert a selected transgene into the multleaf spinach of the invention or may, alternatively, be used for the preparation of transgenes which can be introduced by backcrossing. Methods for the transformation of plants, including spinach, are well known to those of skill in the art.

Vectors used for the transformation of spinach cells are not limited so long as the vector can express an inserted DNA in the cells. For example, vectors comprising promoters for constitutive gene expression in spinach cells (e.g., cauliflower mosaic virus 35S promoter) and promoters inducible by exogenous stimuli can be used. Examples of suitable vectors include pBI binary vector. The "spinach cell" into which the vector is to be introduced includes various forms of spinach cells, such as cultured cell suspensions, protoplasts, leaf sections, and callus. A vector can be introduced into spinach cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target spinach cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including multileaf trait spinach of the invention.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including spinach plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for spinach plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from spinach (psaD, psaF, psaE, PC, FNR, atpC, atpD, cab, rbcS) (see U.S. Pat. No. 7,161,061), the CAB-1 promoter from spinach (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the multileaf trait spinach of this invention include, for example, DNA sequences or genes from another species, or even genes or sequences which originate with or are present in spinach species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a multileaf trait spinach plant according to the invention. Non-limiting examples of particular genes and corresponding phenotypes one may choose to introduce into a spinach plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pats. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above RELATED APPLICATIONS & INCORPORATION BY REFERENCE section, are additionally cited as examples of U.S. patents that may concern transformed spinach and/or methods of transforming spinach or spinach plant cells, and techniques from these US patents, as well as promoters, vectors, etc., may be employed in the practice of this invention to introduce exogenous nucleic acid sequence(s) into the multileaf trait spinach (or cells thereof) of the invention, and exemplify some exogenous nucleic acid sequence(s) which can be introduced into the multileaf spinach (or cells thereof) of the invention, as well as techniques, promoters, vectors etc., to thereby obtain further multileaf trait spinach plants, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

Propagation Material

The invention further relates to propagation material for producing plants of the invention. Such propagation material comprises inter alia seeds of the claimed plant and parts of the plant that are suitable for sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems. (See generally U.S. Pat. No. 7,041,876 on spinach being recognized as a plant that can be regenerated from cultured cells or tissue).

Morphological and Physiological Characteristics

According to another aspect of the invention *Spinacia oleracea* plants are provided that have all of the morphological and physiological characteristics corresponding to the multileaf trait of multileaf spinach plants of the invention, representative seed of which having been deposited under NCIMB Accession No. NCIMB 41619, which plants are grown from seeds of a plant of the invention or regenerated from parts thereof, or from a tissue culture. Plants of the invention should have the morphological and physiological characteristics that correspond with the multileaf trait but do not necessarily have all the other characteristics of plants of the deposited seeds. The trait is broadly transferrable over multiple spinach types and varieties.

Progeny

The invention also relates to progeny of the spinach plants of the invention. Such progeny can be produced by sexual or vegetative reproduction of a plant of the invention or a progeny plant thereof. The regenerated progeny plant shows the multileaf characteristic in the same or a similar way as the plant, of which representative seed was deposited (NCIMN 41619). This means that such progeny has the same characteristics as claimed for the spinach plants of the invention. In addition to this, the plant may be modified in one or more other characteristics. Such additional modifications are for example effected by mutagenesis or by transformation with a transgene or cisgene. Alternatively, modifications in characteristics other than the multileaf trait can be introduced by introducing the multileaf trait in a different background.

As used herein the word "progeny" is intended to mean the offspring or the first and all further descendants from a cross with a plant of the invention that shows multileaf characteristics. Progeny of the invention are descendants of any cross with a plant of the invention that carries the multileaf trait.

"Progeny" also encompasses plants that carry the trait of the invention which are obtained from other plants of the invention by vegetative propagation or multiplication.

In one embodiment, the progeny plant has all of the morphological and physiological characteristics of the claimed plant in respect of the multileaf trait, representative seed of which having been deposited under accession number NCIMB 41619. Such progeny has the same multileaf characteristics as claimed for the plant of the invention and may be modified in one or more other characteristics.

Cells, Plants, Seed, Germplasm and Leaves

The invention further relates to cells of multileaf spinach plants as described herein. The cells comprise the genetic information that leads to the multileaf trait as described herein. Suitably, this genetic information is substantially identical, preferably completely identical to the genetic information encoding the multileaf trait of plants that have all of the morphological and physiological characteristics pertaining to the multileaf trait of multileaf spinach plants of the invention, representative seed of which having been deposited under accession number NCIMB 41619. Preferably, the cell of the invention is part of a plant or plant part, but the cell may also be in isolated form.

In an embodiment the plants of the invention are plants grown from seeds having the deposit accession number NCIMB 41619.

In an embodiment the plants of the invention are progeny plants of plants grown from seeds having the deposit accession number NCIMB 41619 that carry the multileaf trait.

In an embodiment the plants of the invention are plants that carry in their genome the genetic information that is responsible for the multileaf trait by causing the plant to form significantly more leaves than a plant not having the said genetic information in its genome.

The spinach plants according to the invention may be of the following types: savoy, semi-savoy and smooth or any other type.

The invention, furthermore, relates to hybrid seed and to a method of producing hybrid seed comprising crossing a first parent plant with a second parent plant and harvesting the resultant hybrid seed. In order for the hybrid seed to express the trait of the invention, both parent plants need to be homozygous for the multileaf trait but not necessarily uniform for other traits.

The invention also relates to the germplasm of plants of the invention. The germplasm is constituted by all inherited characteristics of an organism and according to the invention encompasses at least the multileaf trait of the invention.

The invention also relates to the multileaf spinach leaves that are produced by the plants of the invention and marketed as vegetables, either as fresh vegetables or processed, i.e. cooked, and optionally frozen.

The invention further relates to a container comprising one or more plants of the invention in a growth substrate for harvest of leaves from the plant in a domestic environment. This way the consumer can pick very fresh leaves for use in salads. More generally, the invention includes one or more plants of the invention wherein the plant is in a ready-to-harvest condition, including with the consumer picking his own, and further including a container comprising one or more of these plants.

"Multileaf Trait" and "Significantly More"

In this specification the term "multileaf trait" is intended to mean having the genetic information that in homozygous state leads to the plant growing 1.25 times as many leaves as the same spinach plant not having the said genetic information and which trait is as found in plants of which representative seeds were deposited under accession number NCIMB 41619, in particular in plants grown from the deposited seeds. "The same spinach plant" is in particular a plant having the same genetic background, for example a non-multileaf plant as found in an F2 population that segregates for the multileaf trait.

"Significantly more" is in one embodiment at least 1.25 times the number of leaves of a plant that does not carry the genetic information responsible for the multileaf trait. In one embodiment significantly more is at least 1.5 times, in particular at least 2 times the number of leaves. In one embodiment significantly more is 2.5 times the number of leaves.

The present invention will be further illustrated in the examples that follow and which are not intended to limit the invention in any way.

EXAMPLES

Example 1

The Multileaf Trait

Figure 1:
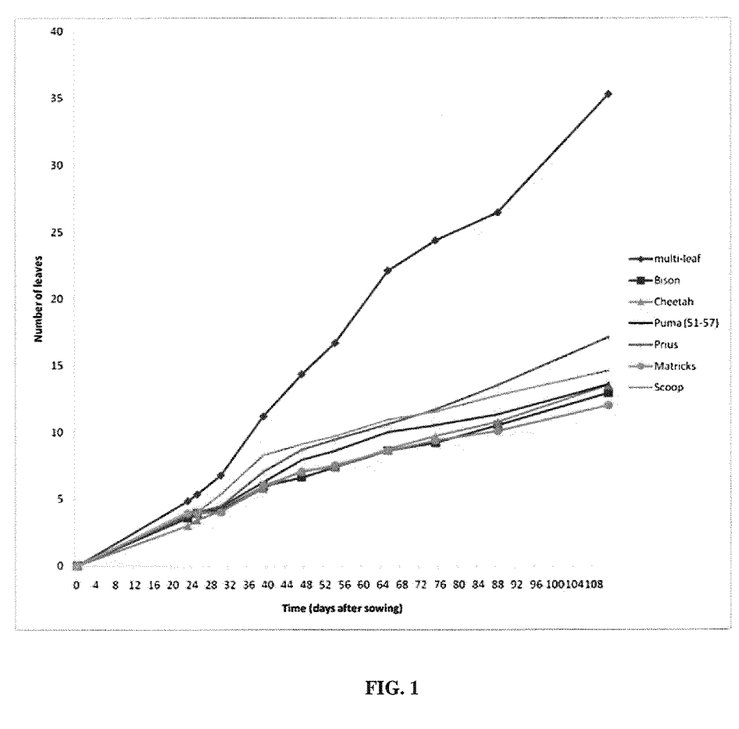
FIG. 1 shows the number of fully developed leaves as a function of time of plants of the invention in comparison with spinach plants not having the multileaf trait.

Plants of the invention were obtained by growing seeds that have the multileaf characteristic as found in seeds that were deposited under accession number NCIMB 41619. Seeds were sown on 5 cm plant cubes and allowed to germinate under greenhouse conditions. After 6 days germinated plants were transferred to a cabrio greenhouse (October 2009, allowing typical frost-free fall-specific growth). Three weeks after sowing plants were transplanted to pots with a diameter of 12 cm and the number of leaves were counted at several time points during development. Plants of different commercially available spinach varieties (Bizon (RZ), Cheetah (RZ), Puma (51-57) (RZ), Rhino (RZ), F1 Prius (Seminis), Matricks (Sumito) and F1 Scoop (Seminis) were grown under the same conditions. Of each group 12 plants were monitored for a period of 16 weeks and the average number of leaves per plant were calculated for each time point (from 8 October to end December 2009) The results are shown in FIG. 1.

Figure 2:
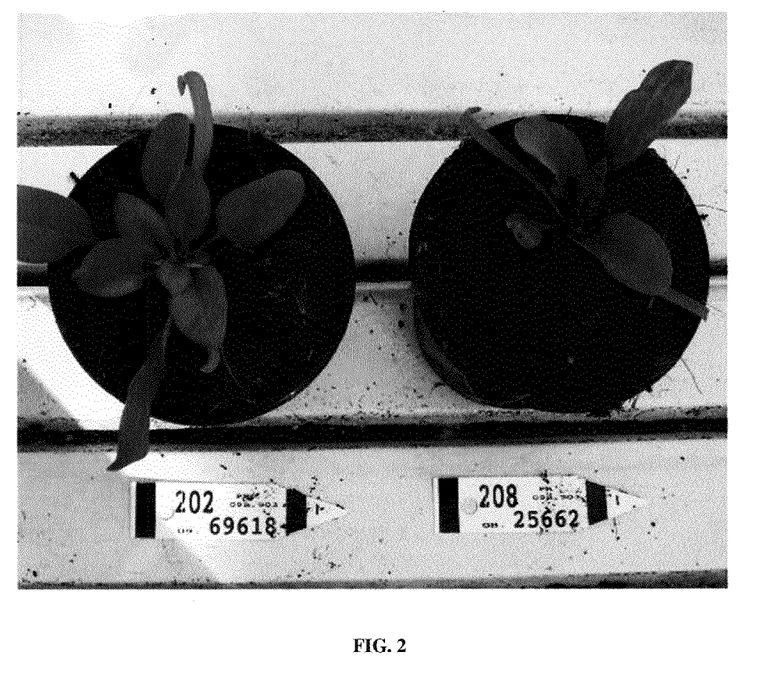
FIG. 2 shows a comparison between a plant of the invention (left) and a prior art plant.
Figure 3:
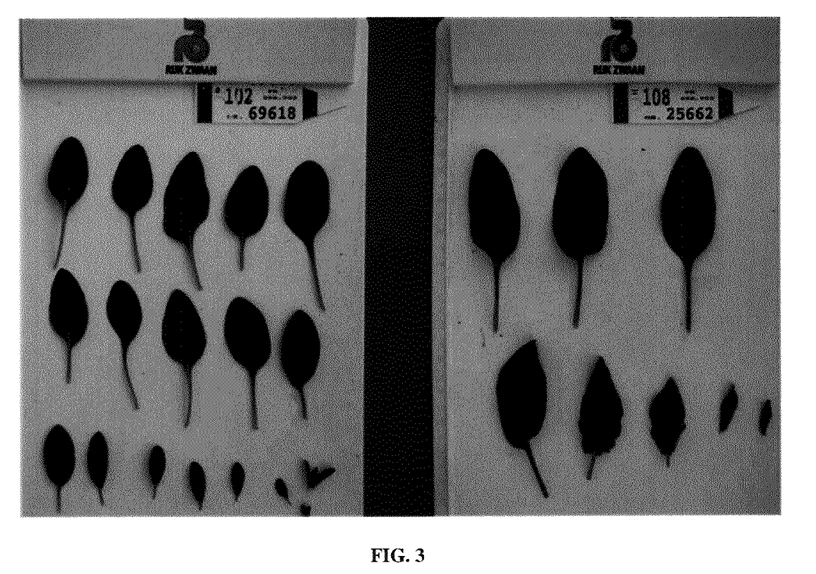
FIG. 3 shows the separate leaves of a plant of the invention (left) and a prior art plant (Matricks)—both of which were grown under the same conditions.

FIG. 2 shows the comparison between a plant of the invention (202) and a prior art spinach plant of the cultivar Matricks (208, both grown under identical greenhouse conditions). It is clearly visible that the spinach plant of the invention has more leaves than Matricks The same difference is shown in FIG. 3. The left panel shows all the leaves of a plant of the invention (102) and the right panel shows all the leaves of a Matricks plant (108). The plant of the invention has significantly more leaves. Again both were grown in identical conditions and growth period.

Example 2

Introduction of the Multileaf Trait into Other Plants

A plant of the invention was crossed with a plant that does not contain the multileaf trait to obtain an F1. The F1 was selfed to obtain an F2. All F2 plants were sown directly in the field in Fijnaart during fall 2009, the Netherlands.

Figure 4:
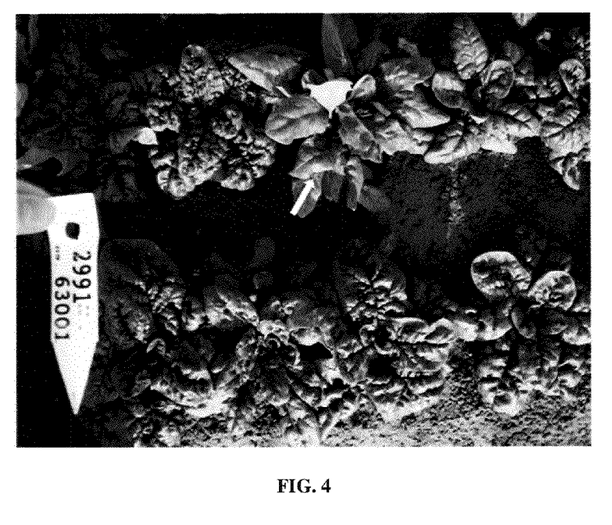
FIG. 4 shows the phenotypes of segregating F2 plants, containing plants that express the multileaf trait and plants that do not show the multileaf trait.

FIG. 4 shows F2 plants from a cross with a plant carrying the multileaf trait. The plant marked with white arrowhead shows the multileaf phenotype, the other plants are from the same population but are not exposing the trait. Plants were sown directly in the field (fall 2009, Fijnaart, the Netherlands). The multileaf trait segregates in the F2 in a fashion that fits with recessive inheritance.

The invention is further described by the following numbered paragraphs

1. A spinach plant which carries the multileaf trait and has at least 1.25 times as many leaves as a plant not carrying the multileaf trait wherein said trait is obtainable by introgression from a multileaf spinach plant representative seed of which was deposited with the NCIMB under accession number NCIMB 41619.
2. Spinach plant as in paragraph 1, which carries the multileaf trait and has at least 1.25 times as many leaves as a plant not carrying the multileaf trait wherein said trait is introgressed from a multileaf spinach plant representative seed of which was deposited with the NCIMB under accession number NCIMB 41619.
3. Spinach plant as in paragraph 1 or 2, which plant has at least 1.5 times as many leaves as a plant not carrying the multileaf trait.
4. Spinach plant as in paragraph 1 or 2, which plant has at least 2 times as many leaves as a plant not carrying the multileaf trait.
5. Spinach plant as in paragraph 1, 2 or 3, which plant has at least 2½ times as many leaves as a plant not carrying the multileaf trait.
6. A spinach plant comprising the multileaf trait as in any one of paragraphs 1-5, obtainable by crossing a first spinach parent plant with a second spinach parent plant that has the multileaf trait as found in plants of which representative seed was deposited under deposit accession number NCIMB 41619 to obtain an F1, subsequently selfing plants of the F1 to obtain an F2 and selecting plants from the F2 that have the multileaf trait as plants of the invention.
7. Progeny plant of a spinach plant as in any one of paragraphs 1-6.
8. Propagation material suitable for producing a spinach plant as in any one of paragraphs 1-7, wherein the propagation material is selected from seeds, parts of the plant that are suitable for sexual reproduction, in particular microspores, pollen, ovaries, ovules, embryo sacs and egg cells, parts of the plant that are suitable for vegetative reproduction, in particular cuttings, roots, stems, cells and protoplasts, tissue cultures of regenerable cells, parts of the plant that are suitable for preparing tissue cultures, in particular leaves, pollen, embryos, cotyledon, hypocotyls, meristematic cells, roots, root tips, anthers, flowers, seeds and stems, wherein the plant produced from the propagation material carries the multileaf trait and has at least 1.25 times as many leaves as a plant not carrying the multileaf trait.
9. Spinach plant produced from the propagation material as in paragraph 8 which carries the multileaf trait and has at least 1.25 times as many leaves as a spinach plant not carrying the multileaf trait.
10. Spinach plant as in paragraph 9, wherein cells of the plant contain genetic material encoding the multileaf trait.
11. Cell of a spinach plant as in any one of paragraphs 1-7 and 9-10, which cell comprises genetic information encoding the multileaf trait which genetic information leads to the spinach plant having at least 1.25 times as many leaves as a spinach plant not carrying the multileaf trait, in particular genetic information which is substantially identical, preferably completely identical to the genetic information encoding the multileaf trait of spinach plants that have all of the morphological and physiological characteristics of multileaf spinach plants, representative seed of which having been deposited under NCIMB Accession No. NCIMB 41619.
12. Cell as in paragraph 11, which cell is part of a spinach plant.
13. Container comprising one or more spinach plants as claimed in any one of paragraphs 1-7 and 9-10 in a growth substrate for harvest of leaves from the spinach plant in a domestic environment.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A *Spinacia oleracea* (spinach) plant having genetic information for expressing a multileaf trait
   that segregates in the F2 population in a fashion that fits with recessive inheritance such that when the spinach plant is homozygous as to the genetic information, the spinach plant expresses the multileaf trait
   wherein, under the same environmental conditions, at the vegetative plant stage, in that F2 population, the spinach plant expressing the multileaf trait grows at least 1.25 times as many leaves as another spinach plant of that same population that is not homozygous as to the genetic information for expressing the multileaf trait,
   wherein the genetic information for expressing the multileaf trait is as in a multileaf trait spinach, representative seed having been deposited under NCIMB Accession No. NCIMB 41619.

2. The spinach plant of claim 1 grown from a seed having been deposited under NCIMB Accession No. NCIMB 41619.

3. The spinach plant of claim 1 wherein the multileaf trait includes that, under the same environmental conditions, at the vegetative plant stage, in that F2 population, the spinach plant expressing the multileaf trait grows at least 1.50 times as many leaves as another spinach plant of that same population that is not homozygous as to the genetic information for expressing the multileaf trait.

4. The spinach plant of claim 3 wherein the multileaf trait includes that, under the same environmental conditions, at the vegetative plant stage, in that F2 population, the spinach plant expressing the multileaf trait grows at least 2 times as many leaves as another spinach plant of that same population that is not homozygous as to the genetic information for expressing the multileaf trait.

5. The spinach plant of claim 4 wherein the multileaf trait includes that, under the same environmental conditions at the vegetative plant stage, in that F2 population, the spinach plant expressing the multileaf trait grows at least 2.5 times as many leaves as another spinach plant of that same population that is not homozygous as to the genetic information for expressing the multileaf trait.

6. The spinach plant of claim 1 wherein the multileaf trait is obtainable by introgression from a multileaf spinach plant, representative seed having been deposited under NCIMB Accession No. NCIMB 41619.

7. The spinach plant of claim 1 wherein the trait is introgressed from a multileaf spinach plant, representative seed having been deposited under NCIMB Accession No. NCIMB 41619.

8. The spinach plant of claim 6 obtainable by crossing a first spinach plant with a second spinach plant that has the multileaf trait as found in a multileaf spinach plant, representative seed having been deposited under NCIMB Accession No. NCIMB 41619 to obtain an F1, selfing plants of F1 to obtain F2 and selecting plants from the F2 that have the multileaf trait.

9. The spinach plant of claim 7 obtained by crossing a first spinach plant with a second spinach plant that has the multileaf trait as found in a multileaf spinach plant, representative seed having been deposited under NCIMB Accession No. NCIMB 41619 to obtain an F1, selfing plants of F1 to obtain F2 and selecting plants from the F2 that have the multileaf trait.

10. The spinach plant of claim 9, wherein the plant of multileaf trait spinach is the female parent.

11. A progeny plant, having the multileaf trait, of the spinach plant of any one of claims 1 or 3-10 having the multileaf trait.

12. A propenyl plant, having all the morphological and physiological characteristics of a multileaf trait spinach plant, of the spinach plant of any one of claims 1 or 3-10, representative seed having been deposited under NCIMB Accession No. NCIMB 41619.

13. Propagation material from which the spinach plant of any one of claims 1, 3, 4 or 5 can be produced.

14. A spinach plant produced from the propagation material of claim 13 having the multileaf trait.

15. A spinach plant produced from the propagation material of claim 13, having all the morphological and physiological characteristics of a multileaf trait spinach plant, representative seed having been deposited under NCl MB Accession No. NCIMB 41619.

16. A cell of the spinach plant of any one of claims 1, 2, 3, 4 or 5, containing genetic information encoding the multileaf trait.

17. A part of a multileaf spinach plant comprising the cell of claim 16.

18. A plant part of the spinach plant of any one of claims 1, 2, 3, 4 or 5.

19. The plant part of claim 18, wherein said part is selected from the group consisting of microspores, pollen, ovaries, an ovule, embryo sac, and a cell.

20. A seed of the spinach plant of any one of claims 1, 2, 3, 4 or 5 wherein a plant from the seed expresses the multileaf trait.

21. The spinach plant of any one of claims 1, 3, 4 or 5 that expresses the multileaf trait.

22. A multileaf trait spinach plant grown from the seed of claim 20, or a part of such plant, wherein the plant has all the physiological and morphological characteristics of the multileaf trait spinach plant grown from seed having been deposited under NCIMB Accession No. NCIMB 41619.

23. A tissue culture of regenerable cells of a spinach plant that expresses the multileaf trait of any one of claims 1, 2, 3, 4 or 5.

24. The tissue culture according to claim 23, comprising cells or protoplasts from a plant part selected from the group consisting of embryos, meristems, cotyledons, pollen, leaves, anthers, roots, root tips, pistil, flower, seed and stalks.

25. A multileaf trait spinach plant regenerated from the tissue culture of claim 23, wherein the regenerated plant expresses all of the physiological and morphological characteristics of multileaf trait spinach, representative seed having been deposited under NCIMB Accession No. NCIMB 41619.

26. A method of producing spinach seed, wherein a spinach plant grown from the spinach seed express the multileaf trait, said method comprising crossing the plant of claim 21 with a second spinach plant that expresses the multileaf trait.

27. An $F_1$ hybrid seed produced by the method of claim 26.

28. An $F_1$ hybrid plant produced by growing the seed of claim 27.

29. A seed that produces the plant of any one of claims 1, 3, 4 or 5.

30. A progeny plant of the plant of claim 21 that has the multileaf trait.

31. A progeny plant of the plant of claim 21 that comprises all of the physiological and morphological characteristics of multileaf trait spinach, representative seed having been deposited under NCIMB Accession No. NCIMB 41619.

32. A method of determining the genotype of the plant of claim 21 or a first generation progeny thereof, comprising obtaining representative nucleic acids from said plant and detecting in said nucleic acids a plurality of polymorphisms.

33. The method of claim 32, further comprising the step of storing the results of detecting the plurality of polymorphisms on a computer readable medium.

34. A method of producing multileaf trait spinach comprising collecting multileaf trait spinach from the plant of claim 21, wherein the plant has been cultivated to maturity.

35. A method for producing spinach leaves as a fresh vegetable comprising packaging leaves of a plant of claim 21.

36. A method for producing spinach leaves as a processed food comprising processing leaves of a plant of claim 21.

37. One or more spinach plants of claim 21, in a container, for harvest of leaves.

38. A method for producing a seed of a multileaf trait-derived spinach plant comprising the steps of:
   (a) crossing a spinach plant of claim 21, with a second spinach plant;
   (b) whereby seed of multileaf trait-derived spinach plant form.

39. The method of claim 38, further comprising the steps of:
   (c) crossing a plant grown from said multileaf trait-derived spinach seed with itself or a second spinach plant to yield additional multileaf trait-derived spinach seed;
   (d) growing said additional multileaf trait-derived spinach seed of step (c) to yield additional multileaf trait-derived spinach plants; and
   (e) repeating the crossing and growing steps of (c) and (d) to generate further multileaf trait-derived spinach plants.

40. A method of vegetatively propagating a spinach plant expressing the multileaf trait comprising the steps of:
   (a) collecting tissue capable of being propagated from the spinach plant of claim 21;
   (b) cultivating said tissue to obtain proliferated shoots; and (c) rooting said proliferated shoots to obtain rooted plantlets.

41. The method of claim 40, further comprising growing plants from said rooted plantlets.

42. A method of introducing a desired trait into progeny of a spinach plant that expresses the multileaf trait comprising:
(a) crossing the spinach plant of claim 21 with a second spinach plant that comprises the desired trait to produce FI progeny;
(b) selecting an F1 progeny that comprises the desired trait;
(c) crossing the selected F1 progeny with the spinach plant of claim 21 to produce backcross progeny;
(d) selecting backcross progeny comprising the desired trait and the multileaf trait; and
(e) repeating steps (c) and (d) three or more times in succession to produce selected fourth or higher backcross progeny that comprise the desired trait and the multileaf trait.

43. A multileaf trait spinach plant produced by the method of claim 42.

44. A method of producing a spinach plant expressing the multileaf trait and another desired trait comprising introducing a transgene conferring the desired trait into progeny of the spinach plant of claim 21 wherein the progeny expresses the multileaf trait.

45. A method for producing a seed of a multileaf trait-derived spinach plant comprising the steps of:
(a) crossing the spinach plant of any one of claims 1-5 with a second spinach plant;
(b) whereby seed of multileaf trait-derived spinach plant form.

46. The method of claim 45, further comprising the steps of:
(c) crossing a plant grown from said multileaf trait-derived spinach seed with itself or a second spinach plant to yield additional multileaf trait-derived spinach seed;
(d) growing said additional multileaf trait-derived spinach seed of step (c) to yield additional multileaf trait-derived spinach plants; and
(e) repeating the crossing and growing steps of (c) and (d) to generate further multileaf trait-derived spinach plants.

47. A method of vegetatively propagating a spinach plant containing genetic information for expressing the multileaf trait comprising the steps of:
(a) collecting tissue capable of being propagated from the spinach plant of any one of claims 1-5;
(b) cultivating said tissue to obtain proliferated shoots; and
(c) rooting said proliferated shoots to obtain rooted plantlets.

48. The method of claim 47, further comprising growing plants from said rooted plantlets.

49. A method of introducing a desired trait into progeny of a spinach plant containing genetic information for expressing the multileaf trait comprising:
(a) crossing the spinach plant of any one of claims 1-5 with a second spinach plant that comprises the desired trait to produce F1 progeny;
(b) selecting an F1 progeny that comprises the desired trait;
(c) crossing the selected F1 progeny with the spinach plant of any one of claims 1-5 to produce backcross progeny;
(d) selecting backcross progeny comprising the desired trait and the multileaf trait; and
(e) repeating steps (c) and (d) three or more times in succession to produce selected fourth or higher backcross progeny that comprise the desired trait and the multileaf trait.

50. A multileaf trait spinach plant produced by the method of claim 49.

51. A method of introducing a desired trait into progeny of a spinach plant containing genetic information for expressing the multileaf trait comprising introducing a transgene conferring the desired trait into progeny of the spinach plant of any one of claims 1-5.

52. A tissue culture of regenerable cells of the spinach plant of any one of claims 1, 2, 3, 4 or 5.

53. A multileaf trait spinach plant regenerated from the tissue culture of claim 52.

54. A spinach plant produced from propagation material produced from a plant of claim 2, said spinach plant, having an the morphological and physiological characteristics of a multileaf trait spinach plant, representative seed having been deposited under NCIMB Accession No. MCIMB 41619.

55. A method of producing spinach seed, wherein a spinach plant grown from the spinach seed express the multileaf trait, said method comprising crossing the plant of claim 2 with a second spinach plant that expresses the multileaf trait.

56. An $F_1$ hybrid seed produced by the method of claim 55.

57. An $F_1$ hybrid plant produced by growing the seed of claim 55.

58. A progeny plant of the plant of claim 2 that has the multileaf trait.

59. A progeny plant of the plant of claim 2 that comprises all of the physiological and morphological characteristics of multileaf trait spinach, representative seed having been deposited under NCIMB Accession No. NCIMB 41619.

60. A method of determining the genotype of the plant of claim 2 or a first generation progeny thereof, comprising obtaining representative nucleic acids from said plant and detecting in said nucleic acids a plurality of polymorphisms.

61. The method of claim 60, further comprising the step of storing the results of detecting the plurality of polymorphisms on a computer readable medium.

62. A method of producing multileaf trait spinach comprising: collecting multileaf trait spinach from the plant of claim 2, wherein the plant has been cultivated to maturity.

63. A method of producing spinach leaves as a fresh vegetable comprising packaging leaves of the plant of claim 2.

64. A method for producing spinach leaves as a processed food comprising processing leaves of the plant of claim 2.

65. One or more spinach plants of claim 2, in a container, for harvest of leaves.

66. A seed having been deposited under NCIMB Accession No. NCIMB 41619.

\* \* \* \* \*